United States Patent [19]

Krasnicki et al.

[11] Patent Number: 4,945,913
[45] Date of Patent: Aug. 7, 1990

[54] SINGLE CHAMBER ACOUSTICAL TONOMETER

[75] Inventors: Edward J. Krasnicki, Skaneateles, N.Y.; Donald L. Margolis, Davis, Calif.

[73] Assignee: Welch Allyn, Inc., Skaneateles Falls, N.Y.

[21] Appl. No.: 248,156

[22] Filed: Sep. 23, 1988

[51] Int. Cl.$^5$ ............................................. A61B 3/16
[52] U.S. Cl. ............................... 128/647; 128/649; 128/739; 128/774
[58] Field of Search ................... 128/645–652, 128/745, 661.06, 676, 739, 773–774; 73/78–79, 645–648, 573

[56] References Cited

U.S. PATENT DOCUMENTS

| | | | |
|---|---|---|---|
| 3,070,087 | 12/1962 | Sittel | 128/649 |
| 3,192,765 | 7/1965 | Keiper | 128/645 |
| 3,308,653 | 3/1967 | Roth | 128/645 |
| 3,545,260 | 12/1970 | Lichtenstein et al. | 128/647 |
| 3,613,666 | 10/1971 | Hobbs. | |
| 3,690,158 | 9/1972 | Lichtenstein et al. | 128/649 |
| 3,763,696 | 10/1973 | Krakau | 128/645 |
| 4,192,317 | 3/1980 | Munnerlyn et al. | |
| 4,217,912 | 8/1980 | Hubmann et al. | 128/739 X |
| 4,771,792 | 9/1988 | Seale | 128/649 X |

OTHER PUBLICATIONS

Hamelink et al., "Ocular Tonometry Through Sonic Excitation and Laser Doppler Velocimetry", *Journal of Biomech. Engr.*, vol. 101, 11-1979, pp. 267-270.
Survey of Ophthalmology, vol. 24, No. 4, Jan.-Feb. 1980, pp. 211-217.

*Primary Examiner*—Angela D. Sykes
*Attorney, Agent, or Firm*—Wall and Roehrig

[57] ABSTRACT

The compliance of human tissue is determined by impinging a target area with acoustical energy over a range of frequencies. The target is dynamically sealed within a chamber and the pressure response produced in the chamber over the frequency range is measured. The characteristic of the frequency response is related directly to the compliance of the target.

13 Claims, 1 Drawing Sheet

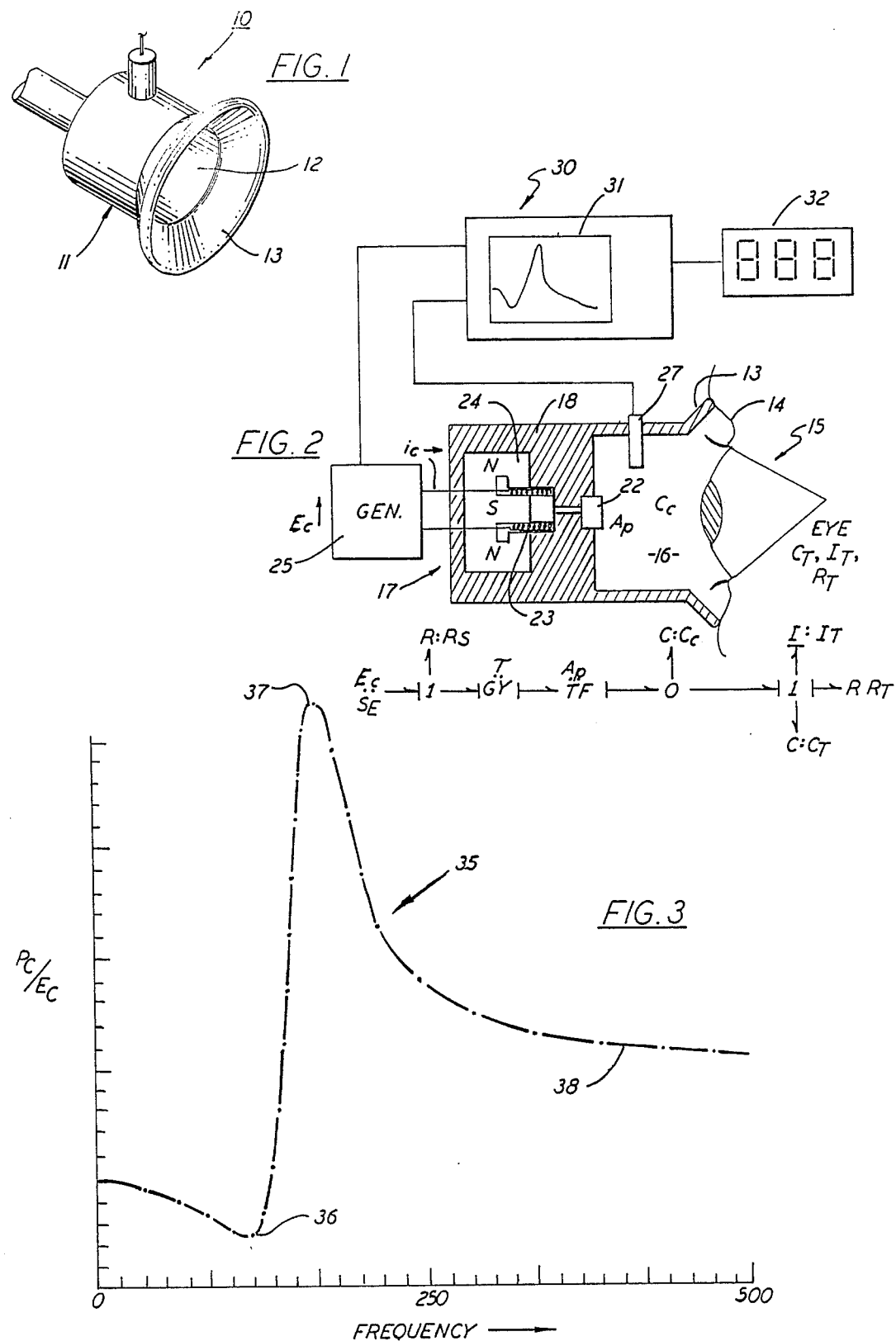

SINGLE CHAMBER ACOUSTICAL TONOMETER

BACKGROUND OF THE INVENTION

This invention relates to tonometry and, in particular, to a non-contact tonometer for determining the health of living tissue.

Tonometry broadly relates to the measurement of tension in living tissue and has special meaning in ophthalmology relating to the intraocular pressure and health of the eye. Pressure in the eye is not measured directly, but is typically inferred by measuring the eye's response to pressure exerted upon the cornea.

One of the most widely employed eye tests is an applanation test devised by H. Goldmann in which the cornea of the eye is flattened by a device having a plane contact surface. The cornea is depressed until the depression reaches a predetermined radius at which time the amount of force required to produce the depression is noted. This force is related to intraocular pressure. By taking pressure readings on a large number of patients, standards have been established for identifying both healthy and glaucomatic eyes. These standards have proven to be reasonably reliable.

The Goldmann applanation and other contact type tests require the test instrument to physically deform the cornea and therefore should only be performed by a physician or a qualified technician to avoid harming and/or stressing of the patient. It is common practice while carrying out an applanation test to anesthetize the patient's eye to minimize discomfort. This, however, poses certain risks in that harmful pressures may be developed in the anesthetized eye.

The accuracy of the applanation tests can be adversely affected by a number of variables. These include the size and shape of the patient's eye, the amount of aqueous humor escaping from the eye when the cornea is depressed, variations in the response of the sclera to the applied pressure, and uncontrolled movement of the patient's head during testing. Attempts to correct or compensate for the effects of these unwanted variables have met with limited success. Furthermore, because the applanation test requires that the instrument physically contact the cornea, potentially harmful microorganisms can enter the patient's body through the eye fluids if the contact surfaces of the instrument are not carefully cleansed.

Lechtenstein, et al. in U.S. Pat. No. 3,545,260 discloses an eye test wherein the compliance of the cornea is used to describe intraocular pressure. In this test, the eye is immersed in a chamber containing a pressurized gas which causes the cornea to become depressed. The depth of the depressure produced by the gas at a given pressure is measured using sound waves. The waves are directed at the deformed region of the eye and the echo return is then time converted to a distance measurement from which intraocular pressure is inferred.

Lechtenstein et al. in a later U.S. Pat. No. 3,690,158 discloses another test in which acoustical energy is used to measure the impedance of the eye. Intraocular pressure is again inferred from these measurements. Here, both the eye under test and a target having a known impedance are immersed in the same liquid media and acoustical waves are directed through the media at both the eye and the target. The measured impedance of the eye is compared to that of the target to determine the health of the eye. It should be noted that a fluid tight seal must be maintained about the patient's eye throughout this test. This type of seal is very difficult to maintain. If the seal is broken or the liquid is disturbed the test results will be erroneous.

OBJECTS AND SUMMARY OF THE INVENTION

It is therefore an object of this invention to improve tonometry and, in particular, tonometers used in measuring the compliance in living tissues.

A still further object of the present invention is to provide a non-contact tonometer that will provide accurate information relating to intraocular pressure.

Another object of the present invention is to provide an acoustical technique for measuring tissue tension in a patient to detect the presence of tumors and other abnormalities.

Yet another object of the present invention is to provide a small hand held instrument, that can be used safely by a patient to take tension readings of the eye and other body areas.

A further object of the present invention is to provide a non-contact tonometer for determining intraocular pressure.

These and other objects of the present invention are attained by dynamically sealing a target containing human tissue within an unobstructive opening to a chamber contained within a housing, acoustically exciting the target over a range of frequencies, measuring the frequency response of the pressure within the chamber, and relating the measured frequency response to the compliance of the target.

BRIEF DESCRIPTION OF THE DRAWING

For a better understanding of these and other objects of the present invention reference is made to the following detailed description of the invention which is to be read in conjunction with the accompanying drawings, wherein:

FIG. 1 is a perspective view of an instrument embodying the teachings of the present invention;

FIG. 2 is a schematic view of the present instrument with an accompanying bond graph representing a model of the instrument wherein termination is provided by a human eye, and FIG. 3 is a response curve showing variations in the instrument chamber pressure over a desired range of frequencies.

BRIEF DESCRIPTION OF THE INVENTION

Turning now to FIG. 1 there is shown an acoustical tonometer, generally referenced 10, that embodies the teachings of the present invention. The instrument includes a cylindrical housing 11 having an unrestricted target opening 12 formed in one end of the housing. An acoustical seal 13 is joined to the housing which is radially disposed about the target opening and protrudes slightly forward from the housing. The seal is formed of a pliable material that can be placed around a given target and pressed into conformity with the surrounding tissue to provide an acoustical or dynamic seal for preventing acoustical energy within a given frequency from escaping from the chamber. The contour of the seal may be preformed to conform to a specific part of the body which, in the case of this preferred embodiment, is the bone structure 14 surrounding a human eye 15 (FIG. 2). FIG. 2 shows the instrument with the eye centered in the opening and the seal in place.

Although the present instrument is ideally well suited for determining intraocular pressure, it can also be used with equal adaptability to determine the compliance or stiffness of other types of tissue. The device can thus be used as a diagnostic instrument for use in early detection of abnormal tissue growth and/or tumors which exhibit a greater amount of stiffness when compared to normal tissue. This type of non-contact diagnosis can be accomplished without having to resort to surgical procedures and therefore reduces the cost involved and eliminates to a great extent patient anxiety.

As seen in FIG. 2, when the present device is used to determine intraocular pressure, the instrument does not deform or in any way make physical contact with the cornea and thus poses little or no risk to the patient. As will be explained below in greater detail, to conduct a diagnostic examination, the seal is simply placed about the target with the target being centered in the opening 12. The target is then acoustically excited over a selected range of frequencies. Pressure variations produced in the chamber 16 are measured and recorded. From these dynamic measurements, the response of the target over the selected frequency range is plotted to provide a characteristic curve relating to the compliance or stiffness of the target. In the case of the eye, intraocular pressure is directly inferred from the dynamic response characteristics.

The term compliance and stiffness may be used synonymously hereinafter with the understanding that compliance is the reciprocal of stiffness. Similarly, the operation of the present invention will be explained with particular reference to diagnosing the health of the human eye. It should be understood, however, that the present instrument may be used to determine the compliance or stiffness of all types of human tissue in the target opening of the instrument without departing from the teachings of the present invention.

As noted above, the present instrument develops valuable information from which intraocular pressure and thus the health of the eye is accurately and directly inferred without having to contact the eye with a probe or the like. Accordingly, the use of local anesthesia is avoided which, in turn, allows for simplified and safer testing when compared to known applanation tests. This non-contact procedure can be repeated at short intervals without danger to the patient and valuable information about changes in the eye's response at various times of the day and night are obtained within a relatively short period of time.

An acoustical driver general reference 17 is mounted in the back wall 18 of the housing opposite the unrestricted opening 12. The driver includes a piston 22 that communicates with a chamber 16 contained within the housing. The piston is coupled to an electrical coil 23 surrounded by a permanent magnet 24. The coil is excited by frequency generator 25 which causes the piston to vibrate linearly through a predetermined range of frequencies to produce pressure fluctuations within the chamber. When testing a human eye, a frequency range of between 0 and 500 Hz has been found to be preferred, however, this range may be varied depending on the nature of the target undergoing diagnostic testing. The frequency generator can be either a wide band noise generator or a sweep generator that is selectively tuned to a desired frequency range. Both of these devices can be purchased from a number of suppliers.

A pressure sensor 27 is mounted within the chamber 16 and is adapted to sense changes in chamber pressure ($P_C$) over the selected range of input frequencies. Pressure related information from the sensor is applied to a spectrum analyzer 30. The analyzer can be any one of many commercially available instruments that are capable of accepting this type of input and providing a visual presentation 31 of the input data over the desired range of frequency. Alternatively, the analyzer may utilize custom circuits that are dedicated to a specific diagnostic application.

A typical characteristic response curve 35 for a human eye undergoing diagnostic testing is shown in FIG. 3. The curve is a plot of pressure related measurements taken by sensor 27 over a frequency range of 0 to 500 Hz. In this case, a ratio of measured chamber pressure ($P_C$) to the exciting voltage ($E_C$) applied to the driver is plotted against frequency to develop the response curve 35. Accordingly, the effects of fluctuations in the driver input voltage are minimized. This curve shows a pronounced minimum peak value 36 at a first frequency and another pronounced maximum peak value 37 at a second higher frequency. After reaching the maximum peak value, the curve drops and becomes asymptotic at a point 38 which represents some definable $P_C/E_C$ value. As can be seen, there are three clearly discernable points on the characteristic curve which, as will be explained in greater detail below, can be used to directly infer the stiffness or compliance of the target.

Eye tests using the present instruments were conducted on both live subjects and enucleated eyes containing pressure taps. It was found in both cases, that the frequency at which the recorded response curve reached a minimum peak was directly related to the compliance of the eye undergoing testing. This relationship was further verified in accordance with the analytical model of the physical system illustrated by the bond graph in FIG. 2. These results also compared favorably with those developed using Goldmann's applanation testing methods.

The eye and other living tissues exhibit a dynamic response similar to a mass-spring-damper system when exposed to excitation at different frequencies. In the present instrument a target located in the target opening 12 is acoustically excited within a range spanning the predictable resonant frequency of the target. Accordingly, as the target oscillates within this range it produces changes in the internal pressure of chamber 16. By measuring the internal pressure of the chamber over the input range of the generator, the frequency at which the target reaches resonance can be accurately and quickly identified. This, of course, occurs at the minimum peak frequency 36. (FIG. 3). It is known that a healthy eye will reach resonance within some definable range of frequencies while an unhealthy eye exhibiting an elevated intraocular pressure will reach resonance at higher frequencies outside of this normal range.

The frequency at which the maximum peak value upon the response curve occurs can also be used as an indicator of target compliance. Here again, an increase in target stiffness causes the maximum peak to move to the right and thus occur at some higher frequency. Changes produced in the maximum peak frequency value by a given target will be different from those produced in the minimum peak frequency value because the frequency at which the curve reaches a peak maximum is influenced by factors other than the resonant behavior of the target. However, this value can be used in the same manner as the minimum peak value to determine the compliance of the target.

The asymptotic values at both the high and low frequency ends of the resonant response curve can also be used as a measure of the targets' resonant behavior. Less compliant or stiffer targets become asymptotic with the abscissa at increasingly high Pc/Ec values. Again, by conducting a sufficient number of tests on different targets, a relationship between these values and target compliance can be established whereby the compliance can be accurately determined.

As illustrated in FIG. 2 the analyzer 31 is equipped with a readout screen that provides a visual presentation of the measured response characteristic curve 35. From this visual presentation direct reading of the key values of interest can be taken to provide the user with a direct indication of the health of the eye. With very little training a patient, or one attending the patient, can monitor the eye at relatively short intervals and quickly note changes in the eye's condition. To further aid the user and provide for ease of reading, the analyzer is equipped with a digital readout 32 that is wired into appropriate analyzer circuits to provide a numerical reading of the minimum peak curve value or any other value of immediate interest. A plurality of readout devices might also be utilized in a similar manner to provide a number of different key readings.

An analytical description of the acoustical tonometer shown in FIG. 2 can be made in association with the bond graph representation of the model also depicted in FIG. 2. The terminator or eye 15 is considered to consist of an inertial effect ($I_T$), a resistive effect ($R_T$) and a compliance effect ($C_T$). The compliance effect is the parameter of greatest interest. The termination effect has been simplified for the purpose of this description but is considered reliable for the model within the noted range of frequencies. It is also assumed for purposes of explanation that both $P_C$ and $E_C$ are measurable values and are thus known variables over the frequency range.

The bond graph variables are represented in a form where the general variable is given first followed by the specific variable, (for example $R{:}R_T$,) relating to the modeled system, wherein:

- R is the generalized variable representing system resistance, $R_S$ is the specific resistance of the coil winding, and $R_T$ is the overall damping resistance associated with the eye.
- C is the general variable representing compliance, $C_C$ is the specific variable relating to the compliance of the chamber and $C_T$ is the specific compliance of the eye.
- I is the generalized variable relating to inertia and $I_T$ is the effective inertia of the eye.
- GY is the generalized system function relating to the gyrator (driver) and $\tau$ is the gyrator modulus relating to the velocity of the voice coil at a specific appllied voltage.
- TF is the generalized variable relating to the transformer function and $A_P$ is the transformer modulus relating to the area of the piston.
- SE is the generalized variable representing the effort source and $E_C$ is the specific effort source.

Laplace transformed state equations are derived directly from the bond graph representation and yield the following transfer function which relates to the chamber pressure ($P_C$) to the driving voltage ($E_C$).

$$\frac{P_C(s)}{E_C(s)} = \frac{\frac{A_P}{T}\frac{1}{C_C}\left[s^2 + \frac{R_T}{I_T}s + \frac{1}{I_T C_T}\right]}{s^3 + \left(\frac{R_T}{I_T} + R_S\left[\frac{A_P}{T}\right]^2 \frac{1}{C_C}\right)s^2 + \left(\frac{R_T}{I_T}R_S\frac{A_P^2}{T}\frac{1}{C_C} + \frac{1}{I_T C_T}s + \frac{1}{I_T C_T}\right)s + \frac{1}{I_T C_T}R_S\left[\frac{A_P}{T}\right]^2 \frac{1}{C_C}}$$

where:
s is the Laplace operator.

From this transfer function a frequency response curve similar to that shown in FIG. 3 can be derived. If $R_T$, the damping associated with the terminator (eye), is small then the minimum frequency peak exists in the frequency response, $$\frac{P_C(j\omega)}{E_C(j\omega)}$$

at:

$$\omega_0^2 = \frac{1}{I_T C_T}$$

where:
$\omega_0$ is the resonant frequency of the eye.

This solution to the numerator of the transfer function for the system demonstrates that the frequency at which the minimum occurs, in the frequency response curve, is directly proportional to the square root of the termination compliance (i.e. stiffness). As can be seen, the frequency at which the minimum occurs changes in response to changes in the intraocular pressure.

Based on the same assumptions, it can be shown that a maximum will occur in the frequency response at $$\omega_n^2 = \omega_0^2\left[1 + \frac{C_T}{C_C}\right]$$

where: $\omega_n$ is the natural frequency of the combined termination and instrument system.

The natural frequency ($\omega_n$) of the eye/instrument system is dependent on the compliance of both the terminator (eye) and the chamber surrounding the termination. With realistic assumptions as to the values of the stated parameters in this eye/instrument system the value of the low frequency asymptote and that at the high frequency asymptote can be used for additional information about the compliance at the termination. If the resistance of the driving voice coil is small, $R_s \rightarrow 0$, then For low frequencies, $s \rightarrow 0$ $$\left[\frac{P}{E_C}\left(\frac{\omega}{\omega_0}\right)\right] \rightarrow \frac{\frac{A_P}{T}\frac{1}{C_C}}{1 + \frac{C_T}{C_C}} = \frac{A_P}{T\omega_0}\frac{1}{C_C + C_T}$$

For high frequencies, $s \rightarrow \infty$ $$\left[\frac{P}{E_C}\left(\frac{\omega}{\omega_0}\right)\right] \rightarrow \frac{A_P}{T} \frac{1}{\omega_0} \frac{1}{C_C}$$

From this relationship it is now evident that it is possible to determine the termination compliance, $C_T$, by measuring the high and low frequency asymptotic behavior of the chamber pressure.

While this invention has been explained with reference to the structure disclosed herein, it is not confined to the details set forth and this application is intended to cover any modifications and changes as may come within the scope of the following claims.

What is claimed is:

1. The method of evaluating the compliance of human tissue that includes
   dynamically sealing a target containing human tissue within a chamber,
   acoustically exciting the target over a given range of frequencies wherein the pressure in the chamber varies in response to resonant behavior of the target,
   measuring the pressure within the chamber over the range of frequencies, and
   relating a measured chamber pressure value directly to the compliance of the target.

2. The method of claim 1 wherein the frequency at which the chamber pressure drops to minimum peak value is related directly to target compliance whereby the higher the minimum peak value the less compliance the target.

3. The method of claim 1 wherein the frequency at which the chamber pressure rises to maximum peak value is related to target compliance whereby the higher the maximum peak value the less compliant the target.

4. The method of claim 1 that includes the further step of generating a frequency response curve by plotting measured chamber pressures against frequency over the given range whereby the characteristics of the curve can be clearly discerned.

5. The method of claim 4 wherein the pressure value of the low frequency asymptote of the curve is related to target compliance.

6. The method of claim 4 wherein the pressure value of the high frequency asymptote of the curve is related to target compliance.

7. The method of claim 1 that includes the further steps of generating acoustical waves within the chamber and directing said waves at the target.

8. The method of claim 1 wherein said target is a human eye and the seal acts against the bone surrounding the eye.

9. Apparatus for determining the compliance of human tissue that includes
   a housing containing an interior chamber and an unobstructed opening for providing an exterior target containing human tissue access to the chamber,
   a dynamic seal surrounding the opening in said housing that is capable of forming an acoustical seal around the target,
   a generator means for producing acoustical waves within the chamber to excite the target over a range of frequencies,
   a sensor means for measuring pressure variations in the chamber over said range of frequencies, and
   analyzer means connected to said sensor means for identifying pressure related values within the range of frequencies that are directly related to target compliance.

10. The apparatus of claim 9 wherein said generator means includes a piston mounted in the chamber and a driver for oscillating the piston to generate acoustical waves within said chamber.

11. The apparatus of claim 10 wherein said analyzer means provides a visual curve showing chamber pressure plotted against the generator means frequency whereby said identifying pressure related values are clearly discernable.

12. The apparatus of claim 9 that further includes readout means for providing a digital presentation of identifying pressure related values.

13. The apparatus of claim 10 wherein said driver is selectably tunable over a desired range of output frequencies.

* * * * *